United States Patent
Shuai

(10) Patent No.: US 11,560,439 B2
(45) Date of Patent: Jan. 24, 2023

(54) HYDROXYPROPYL STARCH FOR PREPARING EMPTY CAPSULES AND HYDROXYPROPYL STARCH-BASED SOFT CAPSULES

(71) Applicant: Hunan Er-Kang Pharmaceutical Co., Ltd., Hunan (CN)

(72) Inventor: Fangwen Shuai, Hunan (CN)

(73) Assignee: Hunan Er-Kang Pharmaceutical Co., Ltd.

( * ) Notice: Subject to any disclaimer, the term of this patent is extended or adjusted under 35 U.S.C. 154(b) by 116 days.

(21) Appl. No.: 16/857,538

(22) Filed: Apr. 24, 2020

(65) Prior Publication Data
US 2021/0332156 A1    Oct. 28, 2021

(51) Int. Cl.
*C08B 31/12* (2006.01)
*A61K 9/48* (2006.01)

(52) U.S. Cl.
CPC .......... *C08B 31/12* (2013.01); *A61K 9/4816* (2013.01); *A61K 9/4833* (2013.01)

(58) Field of Classification Search
CPC ...... C08B 31/12; A61K 9/4833; A61K 9/4816
USPC ........................................ 536/111
See application file for complete search history.

(56) References Cited

U.S. PATENT DOCUMENTS

| | | | | | |
|---|---|---|---|---|---|
| 3,033,853 | A | * | 5/1962 | Klug | ............ C08B 31/12 536/111 |
| 4,804,542 | A | * | 2/1989 | Fischer | ............ A61K 9/4825 424/456 |
| 5,621,088 | A | * | 4/1997 | Gruber | ............ C08B 37/003 536/124 |
| 6,375,981 | B1 | * | 4/2002 | Gilleland | ............ A61K 9/4816 424/451 |

* cited by examiner

*Primary Examiner* — Ganapathy Krishnan
(74) *Attorney, Agent, or Firm* — Lerner, David, Littenberg, Krumholz & Mentlik, LLP

(57) ABSTRACT

This invention comprising in hydroxypropyl starch for preparing empty capsules in alimentary and medical use, and hydroxypropyl starch-based soft capsules. This invention takes water as solvent, mix with propylene epoxide and catalyst for reaction, after washing, drying, hydroxypropyl starch is completed. The MS level of substitution of starch is around 2~5, gelatinization point between 25~60° C. After the hydroxypropyl starch is gelatinized by heating in water, a hydroxypropyl starch matrix soft capsule can be prepared. The invention consists in introducing hydroxypropyl by modifying the molecular chain of starch to improve the flexibility and hydrophilicity of starch. Therefore, a hydroxypropyl starch matrix soft capsule capable of preparing a flexible and disintegrating property is provided.

5 Claims, No Drawings

HYDROXYPROPYL STARCH FOR PREPARING EMPTY CAPSULES AND HYDROXYPROPYL STARCH-BASED SOFT CAPSULES

FIELD OF INVENTION

The invention relates to hydroxypropyl starch used for preparing soft capsules for manufacturing soft capsules used in the fields of food, medicine and hydroxypropyl starch base soft capsules prepared from the hydroxypropyl starch.

BACKGROUND OF THE INVENTION

Capsules, as one of the most widely used dosage forms at present, have the advantages of masking drug taste, high efficacy, controlled release, etc., and have been widely used in medicine, health products, and functional food industries. Traditional capsules generally use gelatin made from animal skin and bone hydrolysis as the capsule shell material. However, gelatin capsules are easy to breed microorganisms, absorb moisture, have poor flexibility, and also have high prices and are not suitable for people with special cultural beliefs. Compared with gelatin capsules, the use of plant materials to prepare capsules can significantly improve the above disadvantages.

As a renewable natural resource, starch has the advantages of rich sources, low prices, and easy biodegradability, and is the most potential substitute for capsule raw materials. However, the original starch does not dissolve in cold water, and the viscosity of the starch paste is unstable. The starch needs to be modified to improve its physical and chemical properties. However, plant capsules formed based on modified starch generally have disadvantages such as complicated operation and greater friability of the capsule, which restricts the large-scale application of starch-based capsule technology. Many researchers use various natural colloids as strengthening and toughening agents, hoping to solve the problem of greater friability of starch capsules. Therefore, it is necessary to provide a modified starch with excellent characteristics and a low cost based on this And small friability plant capsules and preparation method thereof.

Hydroxypropyl starch is a widely used modified starch. It is widely used in food, medicine, paper making, textile, daily chemical, fine chemical, oil field drilling and other industries. Its properties and uses are mainly determined by the degree of modification of starch. That is, the degree of molecular substitution MS. The existing production technologies of hydroxypropyl starch include dry method, water dispersion method and non-aqueous solvent method. Dry production method is the direct gas-solid reaction of starch and propylene oxide under certain conditions. The specific preparation methods mainly include agitation, boiling and extrusion. The dry production reaction has low reaction efficiency, the molecular substitution degree of the obtained product is low, and the product is difficult to separate and purify. Water dispersion method is currently the most widely used technology for the production of hydroxypropyl starch. Its advantages are simple process, easy operation, easy product purification, and high purity products. The disadvantage is that because hydroxypropyl starch is easily swelled and gelatinized in water, it cannot produce products with high degree of substitution. The molecular substitution degree MS of the hydroxypropyl starch obtained by the water dispersion method is not greater than 0.3. The non-aqueous solvent method is to disperse starch in an alcohol or ketone organic solvent and then react with propylene oxide. This method can prepare a higher degree of substitution of hydroxypropyl starch, but the highest degree of molecular substitution of the obtained product is below 2.0. In general, the existing methods for producing hydroxypropyl starch have low production reaction efficiency, the molecular substitution degree of the obtained hydroxypropyl starch is low, uneven, or the product is difficult to separate and purify.

The purpose of the present invention is to overcome and solve the shortcomings and problems of the existing method and technology for producing hydroxypropyl starch, such as low production reaction efficiency, low molecular substitution degree MS of the obtained hydroxypropyl starch, unevenness, and difficulty in product separation and purification. A highly substituted hydroxypropyl starch with high production reaction efficiency, capable of preparing highly substituted MS with excellent flocculation, adhesiveness and surface activity, and easy separation and purification of products Preparation process. At the same time, the present invention consists in introducing a hydroxypropyl group by modifying the molecular chain of the starch to improve the flexibility and hydrophilicity of the starch, thereby providing a hydroxypropyl group with good flexibility and good disintegration properties.

SUMMARY OF THE INVENTION

In view of this, the present invention provides a method for preparing hydroxypropyl starch and soft capsule based on the hydroxypropyl starch.

In order to solve the above problems, the present invention proposes the following technical solutions:

A method for preparing hydroxypropyl starch, comprising the following steps:

(1) Take 1 starch and 3-8 of ethanol into a reaction tank, and stir rapidly to disperse the starch;

(2) Take 0.05~0.2 of the catalyst for the etherification reaction, and slowly add it to the starch dispersion in the reaction tank. During the addition, stir rapidly. After the addition is complete, stir quickly for 20-40 minutes.;

(3) Take 0.1 to 0.3 of propylene oxide and slowly add it to the reaction tank. After the addition is complete, close the reaction tank and continue stirring, then raise the temperature to 30 to 50° C. and control the pressure at 0.1 to 0.3 MPa;

(4) Add the reacted product to cold water at 20 to 25° C., 5 to 10 times the weight of the product, soak and stir for 8 to 10 hours. After the gum is dissolved in water, add a strong acidic cation exchange resin to neutralize, and stir until Its pH is 6.0~7.0, filtered, and the filtrate is a highly substituted hydroxypropyl starch solution;

(5) The hydroxypropyl starch solution was heated in a jacketed open pan, and slowly stirred. As the temperature increased, the solution began to become turbid. When it was heated to 30-60° C., flocculation occurred. Finally, a micelle was formed. The propyl starch gum product is vacuum dried, pulverized, and made into a solid powder product.

Its further technical solution is the method for producing hydroxypropyl starch, characterized in step (1), the starch includes tapioca starch, wheat starch, potato starch, sweet potato starch, corn starch, beans starch, one or more kinds of rice starch.

Its further technical solution is the method for producing hydroxypropyl starch, characterized in step (2), the catalyst comprises one or more kinds of sodium hydroxide or potassium hydroxide, and it needs to be dissolved in water.

Its further technical solution is that the degree of substitution MS of the hydroxypropyl starch (Prepared by the method) is in the range of 2 to 5, and the gelatinization temperature is in the range of 25° C. to 60° C.

A method for producing hydroxypropyl starch soft capsule, including following steps:

(1) Melting: Add the weighed 30%~80% purified water, 5%~30% plasticizer and 20%~60% hydroxypropyl starch into the melting tank and start stirring. The stirring speed is 10 rpm~70 rpm; When the starch is fully dispersed, set the jacket temperature to 90° C.~130° C., the temperature in the tank is 70° C.~110° C., turn on the heating; when the temperature of the material in the tank reaches 85° C.~109° C., turn off the heating. When the temperature is stable, preserve the heat for 10~50 min until the starch is completely gelatinized. After the heat preservation, close all the gas valves on the lid, open the vacuum valve and pump to degas and defoam; First, stir and vacuum for 3 min~10 min, then turn off the stirring and keep vacuuming for 2 min~10 min. After the vacuum, make sure that the vacuum degree in the tank is −0.02 MPa~−0.09 MPa, check the gel mass temperature (70° C.~90° C.) and moisture content (44%~55%); Release the qualified gel mass into holding tank (temperature set to 70° C.~90° C.) and stand-by;

(2) Encapsulation: Before encapsulating, install the melting tank, gel mass delivery pipe of the spreader box, preparing tank, liquid delivery pipe of the chemical-liquid pump, encapsulation main machine and compressed air pipe of the melting tank; open the machine and compressed air valve, heating the spreader box and the delivery pipe, set the temperature of the spreader box to 70° C.~95° C., until the temperature of the spreader box and the gel mass delivery pipe reaches 70° C.~90° C., open the gel mass flow control valve for spreading the gel mass, the speed is 0.5 rpm~5.0 rpm, adjust the ribbons thickness (0.60 mm~0.85 mm), and control the indoor temperature (18° C.~26° C.) and relative humidity (15%~35%); After the ribbons thickness is qualified, lower the wedge, adjust to the proper height, inject the contents, test encapsulating the soft capsules, check the soft capsules' loading capacity, and wait for the filled quantity to reach the target requirements. Pass the encapsulated soft capsules through the delivery belt into the tumblers for forming stage; during the encapsulation, take a sample every 30 minutes to check the volume of the capsules, and check the appearance of the soft capsules at any time;

(3) Drying: The soft capsules that have undergone the forming stage are spread evenly in the tray, and then moved to the drying room to continue drying. The drying time is 10 h~38 h, and the moisture content of the ribbon is controlled between 8% and 15%. During the drying period, turn the sample once in 2 h~6 h, and monitor the relative humidity (15%~35%) and temperature (18° C.~26° C.) in the drying room;

(4) Sorting: Pour the dried soft capsules on a light inspection table to select pills, and remove unsuitable soft capsules such as small and large capsule, special-shaped capsule, cracked capsule, thin-walled capsule, matte capsule, adhesion capsule.

It's further technical solution is the method for producing hydroxypropyl starch soft capsule, characterized in that the plasticizer in step (1) includes one or more of glycerin, sorbitol and polyethylene glycol.

This invention had an in-depth research on soft capsules, which are mainly prepared with hydroxypropyl starch. The invention proposes that introducing hydroxypropyl functional groups on starch molecules can improve the existing defects of the starch matrix, and The propyl modification not only overcomes the intermolecular hydrogen bonding force (To improves the toughness), but also effectively inhibits the retrogradation of starch. At the same time, it also increases the hydrophilic properties of starch molecules and reduces the gelatinization temperature, thus the starch-based soft capsules have good disintegration properties. In conclusion, Compared with hydroxypropyl methylcellulose plant capsules, the starch-based soft capsules prepared by the method have the advantages of easy to shape, rapid disintegration, and low price.

SPECIFIC OPERATION METHOD

Example 1

500 g of tapioca starch, dispersed in 2400 g of ethanol, poured into a sandwich stainless steel reaction tank, and stirred well. Dissolved 30 g of sodium hydroxide in water, then slowly added dropwise to the starch dispersion while rapidly stirring. When finish all the sodium hydroxide drops, continue to stir for 30 minutes. Then add 50 grams of propylene oxide to the reaction tank while stirring. Next, close all the valves of the reaction tank and gradually increase the temperature. After 60 minutes, the temperature was raised to 45° C. and maintain it for 90 minutes. Release cyclohexane from the reaction tank, and transfer the reaction product from the reaction tank to the open pot. Add 5 liters of cold water, stir slowly, and soak overnight. After the reaction product was dissolved, the solution became alkaline. Add H-732 cation exchange resin for neutralization while stirring until the pH of the solution is 6.5. Filter and transfer the filtrate to an open pot. The filter residue is a cation exchange resin. After washing with water, it is regenerated and can be used for the next batch. Use the solution in a hot open pot, stir slowly, and raise the temperature to 45° C. and start flocculation, when the temperature reaches 55° C.~60° C., the liquid will flocculate into micelles. Taking out the micelles, 1630 g of highly substituted hydroxypropyl starch gel was obtained, the dry products was 58.3%, and the molecular substitution degree MS was 3.64.

Example 2

500 grams of corn starch, dispersed in 2500 grams of ethanol. Add the dispersion to a stainless steel reaction tank and stir well. Take 30 grams of sodium hydroxide and dissolve it in water. Cooling down and slowly add it to the starch dispersion while stirring rapidly. Continue stirring for 30 minutes after all the sodium hydroxide were added. 100 grams of propylene oxide was slowly added to the reaction tank while continuously stirring. Then close the valve and increase the temperature. 1 hour later, the temperature was raised to 40° C., and maintain the temperature for 60 minutes. The following operations are in accordance with Example 1: The flocculation temperature was 60-70° C. 1320 g of highly substituted hydroxypropyl starch gel mass were obtained. The dry products was 52.4%, and the degree of molecular substitution degree MS was 2.64.

Example 3

500 g of tapioca starch was dispersed in 2400 g of cyclohexane. The starch dispersion was added to a high-pressure reaction tank and stirred. 40 g of potassium hydroxide was dissolved in water and cooled, and then slowly added dropwise into the reaction tank, and quickly stirred. After the addition, continue to stir rapidly for half an hour. Then add 150 grams of propylene oxide into the tank slowly, while stirring quickly, then close the valve, slowly warm up and continue to stir, raise the temperature to 50° C. within 1 hour and maintain it for 120 minutes. The following operation was carried out according to Example 1: the flocculation gel temperature was 50-60° C., 1880 grams of highly substituted hydroxypropyl starch gel was obtained, the dry product was 48.9%, and the molecular substitution degree MS was 3.98.

Example 4

(1) Melting: Weigh 55% purified water, 5% glycerin, and 40% of the hydroxypropyl starch prepared in Example 1 into a melting tank, and start stirring, the stirring speed is 20 rpm; Fully disperse the starch, and set the jacket temperature to 90° C. and the temperature in the tank to 70° C., turn on the heating; When the temperature of the material in the melting tank reaches 85° C., turn off the heating until the displayed temperature value is stable, preserve the heat for 50 minutes until the starch is completely gelatinized; Then close all the gas valves on the lid of the tank, open the vacuum valve and pump to degas and defoam; First, vacuuming along with stirring for 3 min, then close the propeller and continue vacuuming for 2 min. After vacuuming, make sure the vacuum in the tank is −0.02 MPa, and check the gel mass temperature (70° C.) and moisture content (55%); Release the gel mass that meets the above conditions into a holding tank (temperature set to 70° C.), stand-by;

(2) Encapsulation: Before the Encapsulation, install the gel delivery pipe between the holding tank and the spreading box, install the filling content delivery pipe between the liquid compounding tank and the liquid pump, install the compressed air pipe between the encapsulation machine and the holding tank. Open the compressed air valve and turn on the machine's power, heating the spreading box and gel delivery pipe, set the temperature of the spreading box to 70° C., when the temperature of the spreading box and gel delivery pipe reach 70° C., open the flow controlling valve, start spreading, the rotate speed is 0.5 rpm, adjust rubber thickness (0.60 mm), while controlling the encapsulation room temperature (20° C.) and relative humidity (20%); if the rubber thickness is qualified, lower the spray body to the appropriate height, inject the filling contents, encapsulate the soft capsules and test the filling capacity of the soft capsules. When the quantity of the soft capsules reaches 500 mg/capsule, deliver the soft capsules into the tumbler through the conveyor belt for shaping. During the encapsulation process, check the appearance of soft capsules and get samples every 30 min to check the filling capacity.

(3) Drying: After shaping, the soft capsules should be spread evenly in the tray, and move to the drying room. The drying time is 24 hours, and the moisture content of the capsule shell is controlled at 12%. During the drying period, turn the sample over every 3 hours, and control the relative humidity (20%) and temperature (20° C.) of the drying room.

(4) Sorting: Use a light inspection table to sort soft capsules, and remove unqualified soft capsules, such as small or big capsules, unevenly shaped capsules, shriveled capsules, leaked capsules, thin rubber capsules, non-smooth capsules and adhesion capsules.

The hydroxypropyl starch matrix soft capsules refer to the method prescribed in the "Chinese Pharmacopoeia 2015 Edition" and use a smart disintegrator to perform disintegration experiments. It was tested that all 6 samples could disintegrate within 25 minutes, and the disintegration time meet Pharmacopoeia requirements.

Example 5

(1) Melting: Weigh 45% purified water, 10% polyethylene glycol, and 45% of the hydroxypropyl starch prepared in Example 2 into a melting tank, Start stirring at a speed of 50 rpm; Fully disperse the starch; Set the jacket temperature to 115° C. and the temperature in the tank to 95° C., and turn on the heating; When the temperature of the material in the melting tank reaches 99° C. turn off the heating and when the displayed temperature value is stable, preserve the heat for 20 minutes until the starch is completely gelatinized. Then close all the gas valves on the lid of the tank, open the vacuum valve and vacuum pump to degas and defoam; Vacuuming along with stirring for 10 min, then close the propeller, continue vacuuming for 4 min. After the vacuuming, make sure that the vacuum degree in the tank is −0.05 MPa, and check the temperature of the gel mass (85° C.) and moisture content (48%); Release the gel mass that meets the above conditions into the holding tank (Temperature set to 85° C.), stand-by.

(2) Encapsulation: Before encapsulating, install the melting tank, gel mass delivery pipe of the spreader box, preparing tank, liquid delivery pipe of the chemical-liquid pump, encapsulation main machine and compressed air pipe of the melting tank; open the machine and compressed air valve, heating the spreader box and the delivery pipe, set the temperature of the spreader box to 70° C.~95° C., until the temperature of the spreader box and the gel mass delivery pipe reaches 70° C.~90° C., open the gel mass flow control valve for spreading the gel mass, the speed is 0.5 rpm~5.0 rpm, adjust the ribbons thickness (0.60 mm~0.85 mm), and control the indoor temperature (18° C.~26° C.) and relative humidity (15%~35%); After the ribbons thickness is qualified, lower the wedge, adjust to the proper height, inject the contents, test encapsulating the soft capsules, check the soft capsules' loading capacity, and wait for the filled quantity to reach the target requirements. Pass the encapsulated soft capsules through the delivery belt into the tumblers for forming stage; during the encapsulation, take a sample every 30 minutes to check the volume of the capsules, and check the appearance of the soft capsules at any time;

(3) Drying: The soft capsules that have undergone the forming stage are spread evenly in the tray, and then moved to the drying room to continue drying. The drying time is 10 h~38 h, and the moisture content of the ribbon is controlled between 8% and 15%. During the drying period, turn the sample once in 2 h~6 h, and monitor the relative humidity (15%~35%) and temperature (18° C.~26° C.) in the drying room;

(4) Sorting: Use a light inspection table to sort soft capsules, and remove unqualified soft capsules, such as small or big capsules, unevenly shaped capsules, shriveled capsules, leaked capsules, thin rubber capsules, non-smooth capsules and adhesion capsules.

The hydroxypropyl starch matrix soft capsules refer to the method prescribed in the "Chinese Pharmacopoeia 2015 Edition" and use a smart disintegrator to perform disintegration experiments. It was tested that all 6 samples could disintegrate within 24 minutes, and the disintegration time meet Pharmacopoeia requirements.

Example 6

(1) Melting: Weigh 35% purified water, 15% sorbitol and 50% of the hydroxypropyl starch prepared in Example 3 into a melting tank and start stirring, the stirring speed is 70 rpm; Fully disperse the starch, and set the jacket temperature to 130° C. and the temperature in the tank to 110° C., and turn on the heating; when the material temperature in the melting tank reaches 109° C., turn off the heating and when the displayed temperature value is stable, preserve the heat for 10 minutes until the starch is completely gelatinized; Then close all the gas valves on the lid of the tank, open the vacuum valve and vacuum pump to degas and defoam; Vacuuming along with stirring for 6 min, then close the propeller and continue vacuuming for 10 min. After vacuuming, make sure that the vacuum value in the tank is −0.09 MPa, and check the gel mass temperature (90° C.) and moisture content (44%). Release the gel mass that meets the above conditions into the holding tank (Temperature set to 85° C.), stand-by.

(2) 2) Encapsulation: Before encapsulating, install the melting tank, gel mass delivery pipe of the spreader box, preparing tank, liquid delivery pipe of the chemical-liquid pump, encapsulation main machine and compressed air pipe of the melting tank; open the machine and compressed air valve, heating the spreader box and the delivery pipe, set the temperature of the spreader box to 70° C.~95° C., until the temperature of the spreader box and the gel mass delivery pipe reaches 70° C.~90° C., open the gel mass flow control valve for spreading the gel mass, the speed is 0.5 rpm~5.0 rpm, adjust the ribbons thickness (0.60 mm~0.85 mm), and control the indoor temperature (18° C.~26° C.) and relative humidity (15%~35%); After the ribbons thickness is qualified, lower the wedge, adjust to the proper height, inject the contents, test encapsulating the soft capsules, check the soft capsules' loading capacity, and wait for the filled quantity to reach the target requirements. Pass the encapsulated soft capsules through the delivery belt into the tumblers for forming stage; during the encapsulation, take a sample every 30 minutes to check the volume of the capsules, and check the appearance of the soft capsules at any time;

(3) Drying: After shaping, the soft capsules should be spread evenly in the tray, and move to the drying room. The drying time is 38 hours, and the moisture content of the capsule shell is controlled at 8%. During the drying period, turn the samples over every 6 hours, and control the relative humidity (35%) and temperature (18° C.) of the drying room.

(4) Sorting: Use a light inspection table to sort soft capsules, and remove unqualified soft capsules, such as small or big capsules, unevenly shaped capsules, shriveled capsules, leaked capsules, thin rubber capsules, non-smooth capsules and adhesion capsules.

The hydroxypropyl starch matrix soft capsules refer to the method prescribed in the "Chinese Pharmacopoeia 2015 Edition" and use a smart disintegrator to perform disintegration experiments. It is tested that all 50 samples can disintegrate within 23 minutes, and the disintegration time meet Pharmacopoeia requirements.

The invention claimed is:
1. A method for preparing a hydroxypropyl starch matrix soft capsule, comprising:
(1) taking 1 part of a starch and 3 to 8 parts of an ethanol, placing the starch and the ethanol into a reaction tank, and stirring rapidly to disperse the starch to form a starch dispersion;
(2) taking 0.05 to 0.2 parts of a catalyst for an etherification reaction, and slowly adding the catalyst to the starch dispersion in the reaction tank; wherein during the addition of the catalyst, stirring is done rapidly and after the addition is complete, stirring continues quickly for 20-40 minutes;
(3) taking 0.1 to 0.3 parts of a propylene oxide and slowly add the propylene oxide to the reaction tank; wherein after the addition of the propylene oxide is complete, closing the reaction tank and continue stirring, then raising the temperature in the reaction tank to 30 to 50° C., and controlling the pressure in the reaction tank at 0.1 to 0.3 MPa; wherein the reaction occurs for 0.5 to 2.5 hours to form hydroxypropyl starch;
(4) adding the hydroxypropyl starch to cold water at 20 to 25° C., 5 to 10 times by weight of the reacted product, soaking and stirring for 8 to 10 hours; wherein after a gum of the reacted product is dissolved in water, adding a strong acidic cation exchange resin to neutralize, and stirring until pH is 6.0-7.0 to form a filtrate, and wherein the filtrate is a highly substituted hydroxypropyl starch solution;
(5) heating the hydroxypropyl starch solution in a jacketed open pan, and slowly stirring as the temperature is increased, and the solution becomes turbid heating the hydroxypropyl starch solution to 30-60° C. hydroxypropyl gum product that is vacuum dried and pulverized into a solid powdery product of a hydroxypropyl starch; and
(6) adding 5% to 30% of a plasticizer that comprises one or more of glycerin, sorbitol, and polyethylene glycol; 20% to 60% of the hydroxypropyl starch; and 30% to 80% of purified water to a melting tank for stirring and melting at a gelatinization temperature into a gel mass;
(7) releasing the gel mass into a holding tank, and spreading the gel mass into a ribbon for formation into a hydroxypropyl starch matrix soft capsule.

2. The method according to claim 1, wherein in step (1), the starch is selected from a group consisting of a cassava starch, a wheat starch, a potato starch, a sweet potato starch, a corn starch, a legume starch, a rice, and any combination thereof.

3. The method according to claim 1, wherein in step (2), the catalyst comprises one or more of sodium hydroxide or potassium hydroxide, which needs to be dissolved in water when used.

4. The method according to claim 1, wherein the highly substituted hydroxypropyl starch in step (3) has a molecular substitution degree MS in a range of 2 to 5; and wherein the gelatinization temperature is in a range of 25 to 60° C.

5. A method for preparing a hydroxypropyl starch matrix soft capsule, comprising:
(1) (i) adding a 30% to 80% of purified water, a 5% to 30% plasticizer and a 20% to 60% hydroxypropyl starch to a melting tank, stirring at a speed of 10 rpm to 70 rpm until the starch is fully dispersed, setting a jacket temperature to 90° C. to 130° C., wherein temperature in the tank is 70° C. to 110° C., and heating is turned on, and wherein the plasticizer comprises one or more of glycerin, sorbitol, and polyethylene glycol;
(ii) wherein when temperature of material in the melting tank reaches a temperature range of 85° C. to 109° C., turning off heating; wherein after temperature value is stable within the temperature range, keeping the temperature for 10 min to 50 min until the starch is completely melted;
(iii) wherein after heat preservation is completed, closing a gas valve around a lid, and opening a vacuum valve for defoaming; wherein when vacuuming, first stir and evacuate for 3 min to 10 min, then turn off stirring and continue to vacuum for 2 min to 10 min;

(iv) wherein ensuring that a vacuum pressure in the tank is in a range of 0.02 MPa to 0.09 MPa, and checking the gel mass temperature to ensure the gel mass temperature is between 70° C. to 90° C. and the gel mass has moisture content between 44% to 55%;

(v) putting the gel mass into a holding tank at temperature set to 70° C. to 90° C. and setting aside;

(2) (i) before encapsulating, installing a gel mass delivery pipeline between the holding tank and a spread box of an encapsulation machine, the delivery pipeline disposed between a liquid dispensing tank and a pump; and providing an air compression pipeline between the encapsulation machine and the holding tank;

(ii) heating the spreader box and the delivery pipe, setting temperature of the spreader box to between 70° C. to 95° C. opening a compressed air valve;

(iii) opening a gel mass flow control valve for spreading the gel mass, and setting an encapsulation speed of 0.5 rpm to 5.0 rpm, wherein the gel mass undergoes a forming stage where the gel mass is spread evenly to form ribbons that the soft capsule is formed, and adjusting ribbons thickness to 0.60 mm to 0.85 mm, and controlling ambient temperature to 18° C. to 26° C. and relative humidity to 15% to 35%;

(iv) after ribbons thickness is qualified, lowering a wedge, adjusting to a proper height, injecting contents to form soft capsules, testing encapsulating of soft capsules, checking soft capsules' loading capacity, and waiting for filled quantity to reach target requirements; wherein passing encapsulated soft capsules through the delivery belt into tumblers for drying and further shaping the soft capsules;

(v) wherein during encapsulation, taking a sample every 30 minutes to check volume of capsules, and checking appearance of soft capsules at any time;

(3) evenly spreading the shaped soft capsules in trays, and then moving soft capsules to a drying room to continue drying; wherein the drying time is 10 h to 38 h, and moisture content is controlled between 8% and 15%; wherein during the drying period, turn the sample once in 2 h to 6 h, and monitoring relative humidity at 15% to 35% and temperature at 18° C. to 26° C. in the drying room; and (4) pouring dried soft capsules on a light inspection table to select pills, and removing unsuitable soft capsules such as small and large capsule, cracked capsule, thin-walled capsule, matte capsule, and adhesion capsule.

* * * * *